United States Patent [19]
Doernemann et al.

[11] Patent Number: 4,814,154
[45] Date of Patent: Mar. 21, 1989

[54] METHOD AND APPARATUS FOR THE PREPARATION OF A DISINFECTING FLUID

[75] Inventors: Manfred Doernemann, Frankfurt am Main, Fed. Rep. of Germany; Helmut Reif, Biel/Bienne, Switzerland

[73] Assignee: Degesch GmbH, Frankfurt, Fed. Rep. of Germany

[21] Appl. No.: 50,111

[22] Filed: May 15, 1987

[30] Foreign Application Priority Data

May 30, 1986 [DE] Fed. Rep. of Germany ....... 3618297

[51] Int. Cl.$^4$ ............................................. C01B 25/00
[52] U.S. Cl. .................................................. 423/299
[58] Field of Search ......................................... 423/299

[56] References Cited

U.S. PATENT DOCUMENTS

| | | | |
|---|---|---|---|
| 3,375,074 | 3/1968 | Palmer | 423/299 |
| 3,899,375 | 8/1975 | Palmer | 423/299 |
| 4,725,418 | 2/1988 | Friemel et al. | 423/299 |

FOREIGN PATENT DOCUMENTS

| | | | |
|---|---|---|---|
| 136327 | 5/1960 | U.S.S.R. | 423/299 |
| 2065476 | 7/1981 | United Kingdom | 423/299 |

*Primary Examiner*—John Doll
*Assistant Examiner*—Wayne A. Langel
*Attorney, Agent, or Firm*—Beveridge, DeGrandi & Weilacher

[57] ABSTRACT

The invention relates to a method and apparatus or plant for preparing a disinfestation or disinsection fluid which contains an inert fluid and phosphine obtained from the hydrolysis of a water-decomposable metal phosphide. According to the invention to the inert fluid $H_2O$ is added, the inert fluid/$H_2O$ mixture brought into contact with the metal phosphide for the reaction and the resulting disinfestation fluid separated from the solid reaction residue. The mixture of inert fluid and $H_2O$ is brought to react either in liquid or in gaseous state with the metal phosphide. A simple method of preparing the disinfestation fluid resides in that in an opened pressure container (1) calculated amounts of metal phosphide (2), solidified inert fluid (3) and water ice (4) are layered over each other in that order, the pressure container (1) closed and a temperature equalization with the ambient temperature allowed to take place. After completion of corresponding reactions a gaseous mixture of inert fluid and phosphine can be extracted via an expansion valve (7).

21 Claims, 6 Drawing Sheets

METHOD AND APPARATUS FOR THE PREPARATION OF A DISINFECTING FLUID

The invention relates to a method and an apparatus or plant for preparing disinfestation fluid or fumigant which contains an inert fluid and phosphine, i.e. hydrogen phosphide obtained from the hydrolysis of a water-decomposable metal phosphide.

It is known to use phosphorus hydride, that is phosphine, for disinfestation or disinsection, i.e. pest control of and in supplies of grain foodstuffs. The pests to be controlled are mainly insects but in special cases can also be rodents and the like.

The phosphine necessary for the fumigation or gassing of grain silos, which hereinafter will be taken by way of example as the use, is conventionally produced by the hydrolysis of a water-decomposable metal phosphide, for example magnesium phosphide or aluminium phosphide, with water. For this purpose according to known gassing or fumigation methods preparations containing the metal phosphide are laid out in the silo or introduced into the grain stocks by drilling probes. The preparations then react with the moisture from the grain or the ambient air and liberate the desired phosphine. In various cases in addition forced air circulation is employed to distribute the phosphine over the entire contents of the silo. Since the reaction between the metal phosphide and the water can be very violent, depending on the nature of the metal phosphide and on other parameters such as humidity and the ambient temperature, metal phosphide preparations are employed which deliberately effect a delayed gasification.

Nevertheless, with these preparations even with a gas-tight sealed silo it is not possible to obtain a phosphide concentration constant over a relatively long period. The concentration generally rises rapidly up to a maximum value but then diminishes slowly asymptotically. It has however been found that for example with specific types of insects certain development stages, that is the egg and the pupa stage, require for destruction a higher dose, calculated as the product of gas concentration times time, than the larva stage and the adult insect. If the concentrations reached in the gasifying of the metal phosphide preparation are not retained long enough to kill eggs and pupa as well the latter can survive the gassing and continue to develop afterwards. It is thus of more advantage for the gassing to maintain a specific phosphine concentration constant over a relatively long period than to achieve high brief concentrations. The results of test series with harmful insects have shown that considering the two factors gas concentration and time an increase in the time is incomparably more effective than an increase in the concentration providing that the concentration lies above a certain minimum threshold. Such a fumigation course is not only more effective but requires altogether a substantially smaller amount of the toxic phosphine. This continuous concentration can with suitable fumigation methods be kept so low that even the leakage amounts leaving the silo are not harmful.

For fumigation with constant phosphine content over a relatively long period of time the spreading of metal phosphides developing phosphine is not suitable. Even if the spreading were repeated at short intervals of time it would not be possible to generate a constant phosphine concentration in the silo because the gasification speed, as mentioned above, depends on a number of environmental parameters. Moreover, because of the toxicity, damaging to health, of phosphine it is forbidden to enter a silo in which fumigation is still in progress.

It has therefore already been proposed for fumigation with phosphine constant concentrations to pressurize a gas mixture made from phosphine and nitrogen in storage bottles and to conduct the regulated gas mixture obtained from said bottles on expansion into the silo. The type of fumigation has the additional advantage that in the silo no reaction residues or package residues remain as is the case when metal phosphide preparations are spread. The mixture of phosphine gas not generated in situ with an inert gas is also necessary for the simple reason that phosphine gas readily undergoes spontaneous combustion and is therefore explosive and also tends to spontaneous combustion even in relatively small concentrations in a carrier gas when the latter is expanded. It is therefore obvious not to mix phosphine not with a gas containing oxygen such as air but with an inert gas which does not lead to any immediate reaction with the phosphine.

It is also already known that carbon dioxide in the concentration range of a few volume percent acts as synergist of phosphine and thereby accelerates the killing of the insects and thus permits a reduction of the phosphine concentration.

However, the preparation of a mixture of phosphine and an inert gas is in itself problematical because handling the phosphine is extremely dangerous due to its pronounced tendency to spontaneous combustion. In particular, it is only possible by taking great safety precautions to mix phosphine with an inert gas at the location of the fumigation because the transport of phosphine in pure form is very dangerous and the necessary complicated preparation apparatuses are not easily provided at the location of the fumigation.

The invention is therefore based on the problem of providing a method of producing a disinfestation or disinsection fluid which contains phosphine and an inert fluid and with which it is possible to make the disinfestation fluid not only at central locations without any danger and transport it in suitable containers to the place of use but which method can be carried out as well without excessive apparatus expenditure, either with a stationary or a transportable apparatus, at the place of fumigation itself, and which moreover permits convenient and exact control of the phosphide content in the inert fluid and thus in a safe manner simple maintaining of optimum fumigation conditions.

This problem is solved for a method according to the invention of the type set forth at the beginning in that to the inert fluid $H_2O$ is added, the inert fluid/$H_2O$ mixture is brought into contact with the metal phosphide for the reaction and the resulting disinfestation fluid is separated from the solid reaction residue.

This fundamental procedure in which the inert fluid itself is brought together with the amount, and only that amount, of $H_2O$ regulated as necessary for the phosphide hydrolysis and only this mixture allowed to react with the metal phosphide permits various method variants which can be particularly advantageous individually and are claimed in the subsidiary claims.

It is possible to bring the mixture of inert fluid and $H_2O$ either in the liquid or in the gaseous state to react with the metal phosphide. The reaction in the liquid state can be advantageous when the resulting disinfestation fluid itself is to be introduced into for example steel bottles for further dispatch.

A very simple method for the discontinuous preparation of the disinfestation fluid resides in that in an opened pressure container calculated amounts of metal phosphide, solidified inert fluid and water ice are layered over each other in that order, the pressure container sealed and a temperature equalization with the ambient temperature allowed to take place. The inert fluid disposed above the metal phosphide and first changing to the liquid state slowly absorbs water from the melted water ice and bring said water into contact with the metal phosphide for the reaction. After completion of the reaction a gaseous mixture comprising the inert fluid and phosphine can be withdrawn via an expansion valve.

A continuous variant of this procedure resides in that into a continuous flow of the inert fluid in the liquid state the amount of liquid water necessary for the reaction is injected and said liquid mixture is conducted into a reaction or extraction column containing the metal phosphide. The resulting disinfestation fluid extracted in gaseous form via a decompression or expansion valve can after appropriate concentration reduction by supplying further gaseous inert fluid either be used directly for the fumigation via a suitable pipe distributing system or be deposited by indirect cooling by means of suitable coolant in pressure-resistant steel bottles.

A particularly preferred embodiment of the method according to the invention resides in that inert fluid in the gaseous state is saturated with water vapor. This inert gas charged with moisture is then supplied to the reaction container containing the metal phosphide. By regulating the temperature of the water container in this case an excellent possible regulation is obtained for the amount of water supplied to the reaction chamber because the absorption of water vapor by the inert gas can be regulated by influencing the saturation temperature. In addition, a temperature regulation of the reaction container is convenient. Should the reaction in the reaction container reach an undesired temperature this can easily be detected by a temperature sensor and the state counteracted either by stopping the inert gas delivery, by lowering the temperature in the water container or by direct introduction of expansion-cooled inert gas. In this method variant particularly simple and versatile possibilities are obtained of allowing the reaction process to proceed safely in controlled manner. The resulting disinfestation gas of phosphine and inert gas can be supplied directly to a pipe distributing system for the gassing.

The invention also relates to suitable apparatuses for carrying out the methods claimed.

In conjunction with the examples of embodiment the invention will be explained in detail for the use of carbon dioxide as inert fluid in conjunction with magnesium phosphide. Apart from the synergistic effect mentioned at the beginning for the carbon dioxide the use thereof also has the further advantage that the carbon dioxide partially takes part in the reaction ahd when using magnesium phosphide the reaction residue is magnesium carbonate which is a harmless salt occurring naturally in the form of dolomite. When using carbon dioxide and magnesium phosphide the following reaction equation applies:

$$Mg_3P_2 + 3\ CO_2 + 3\ H_2O \rightarrow 2\ PH_3 + 3\ MgCO_3.$$

In the absence of carbon dioxide or when using another inert gas such as nitrogen magnesium hydroxide results as basic reaction residue.

As already mentioned above, when using carbon dioxide as inert fluid because of the synergistic effect it is possible to work with very low phosphine concentrations in the disinfestation fluid. This is not only advantageous as regards the prevention of combustion of the phosphine but also leads, due to the lower phosphine content, to the disinfestation gas having a less corrosive effect, in particular on metal surfaces. This property of phosphine can be critical on use thereof in the vicinity of electronic apparatuses whose contact surfaces can be corroded by the phosphine.

Hereinafter the invention will be explained in detail with the aid of examples of embodiment in conjunction with a description of the attached drawings; with the aid of the method scheme illustrated further significant method features will be discussed. In the drawings.

EXAMPLE 1

Figure 1:
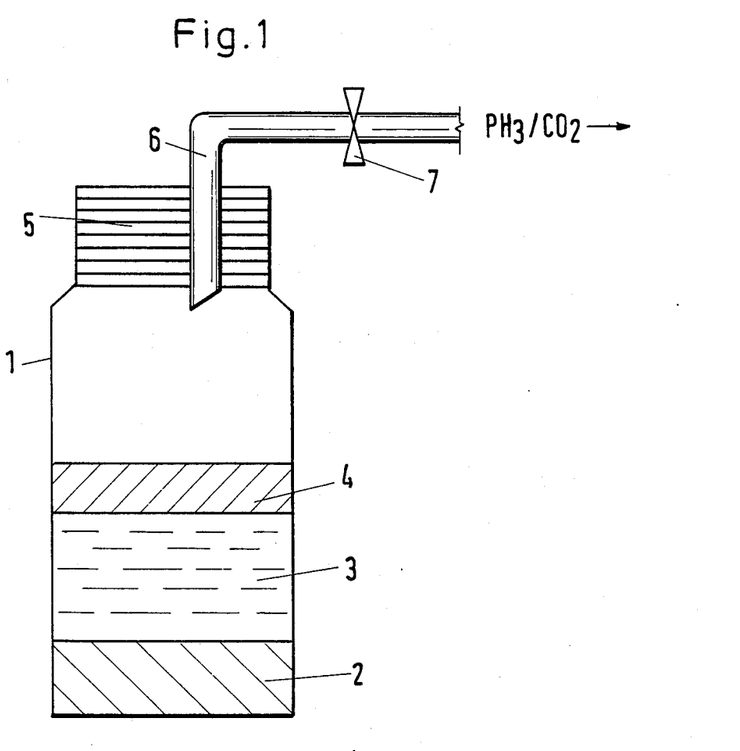
FIG. 1 is a schematic section through a reaction pressure vessel for explaining a discontinuous closed reaction method.

With the reaction arrangement illustrated schematically in FIG. 1 the following test was carried out: Into an opened pressure container 1 of two litres capacity in succession 134 g magnesium phosphide 2, 1000 g carbon dioxide ice 3 and 54 g water ice 4 were introduced in that order and placed in layers over each other. Due to the low temperature of the carbon dioxide ice, which at normal pressure is about −78° C., and the spatial separation of metal phosphide and water ice no immediate hydrolysis reaction takes place. The pressure container 1 was then sealed pressure-tight with a cover 5 which contains an extraction tube 6 provided with an expansion or decompression valve 7. The pressure container thus sealed was left to stand at room temperature for temperature equalization. In the course of the temperature increase firstly the carbon dioxide melts and changes to liquid carbonic dioxide under elevated pressure. At a corresponding temperature the water ice then also starts to melt and liquid water mixes with the carbon dioxide. This mixture then reaches the magnesium phosphide and the hydrolysis reaction specified above is activated. After complete reaction in this test a 7.8% solution of phosphine was contained in carbon dioxide. Said gas can be extracted via the extraction tube 6 and the expansion valve 7 from the pressure container 1. If the extraction tube 6 is not constructed as standpipe and extends into the lower portion of the pressure container 1 the harmless magnesium carbide remains as degassed residue along with any water excess which might be present. Since the vapor pressure of liquid phosphine of about 42 bar is somewhat lower than the vapor pressure of liquid carbon dioxide of about 56 bar, the phosphide content of the disinfestation gas taken from the pressure container and obtained after expansion is lower at the start of the gas extraction than towards the end when the container volume is almost used up. This change in the concentration of the disinfestation gas can if necessary be taken into account by adding proportioned amounts of further gaseous carbon dioxide.

Figure 2:
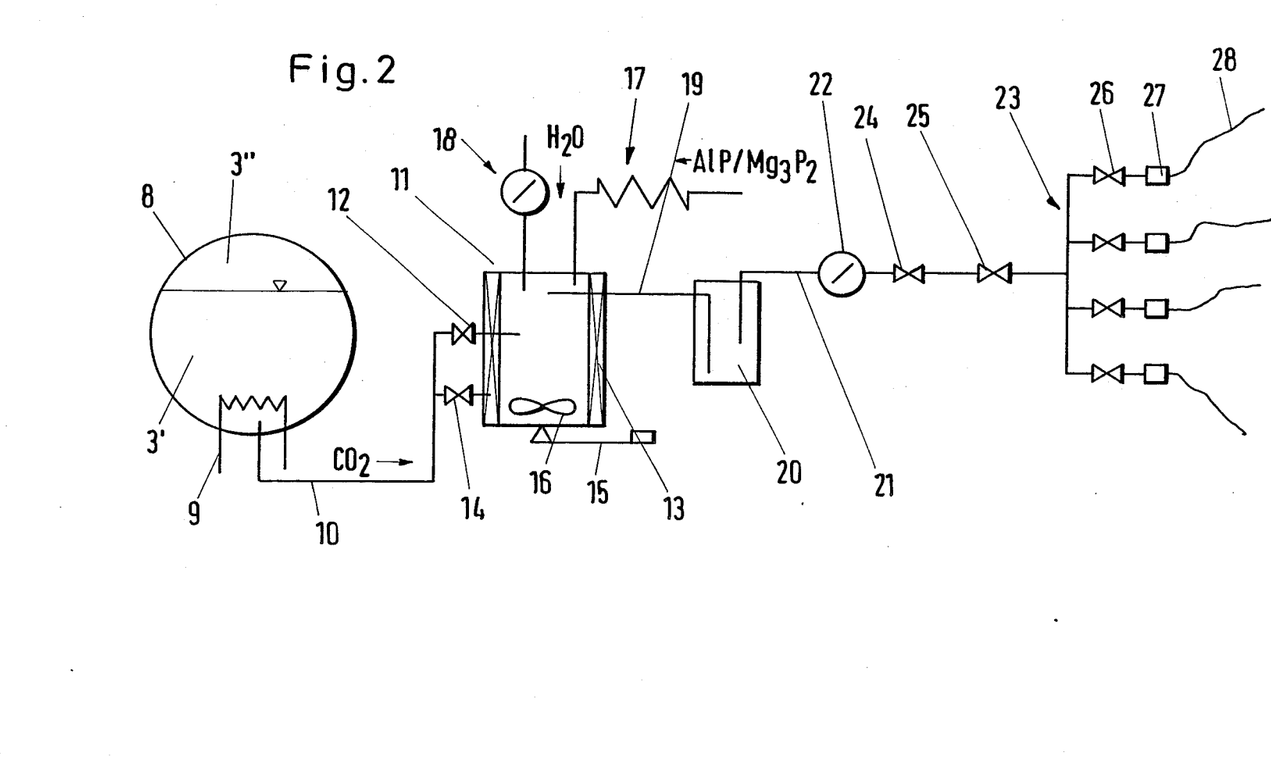
FIG. 2 is a method scheme for the closed reaction method.

FIG. 2 represents a method scheme of an apparatus for carrying out the reaction of example 1. In a supply container 8 liquid carbon dioxide 3' is stored. Depending on the construction of the container the storage is at a pressure between 15 and 70 bar. Above the liquid carbon dioxide 3' there is a gas space containing gaseous carbon dioxide 3". the supply container 8 is provided with a heat-exchange means 9 which can be used when required to enable the liquid carbon dioxide to be set to a desired temperature for the further process. From the lower portion of the supply container 8 a conduit 10 for liquid carbon dioxide leads into a reactor 11. Before the entrance point into the reactor 11 the conduit 10 is provided with an expansion or relaxation valve 12. The reactor 11 also comprises a cooling jacket 13 which can be filled with carbon dioxide via a conduit branching from the conduit 10 with an expansion valve 14.

The reactor 11 rests on a weighing means 15 and is provided in the interior with an agitator 16 which can be used when necessary. At the upper side of the reactor 11 feed means 17 are provided for the phosphide and 18 for water. The feed means 17 for the phosphide is schematically illustrated as feed screw to indicate that here a solid must be introduced into the reactor. The feed means 18 for the water is indicated with a flow meter. Depending on whether filling of the reactor is carried out pressureless or under pressure additionally further corresponding entry locks or-pump means must be provided for the phosphide and the water. If the water is supplied as ice, corresponding means could be associated with the phosphide feed means 17. The resulting disinfestation gas is extracted from the reactor 11 via a conduit 19 which leads to a water separator 20. From here an extraction conduit 21 leads via a quantity meter 22 to a distribution conduit system 23. At 24 and 25 removal connection pieces for a moisture measurement or an analysis means are indicated. The distribution tube system comprises a number of extraction valves 26 to which via couplings 27 fumigation or gassing flexible tubes or hoses 28 can be connected. Said gassing flexible tubes 28 can be connected directly to a container gassing distribution system.

The apparatus illustrated in FIG. 2 is suitable for a discontinuous operation as was described in example 1 but on appropriate modification of the metering and proportioning means can also be operated continuously. Depending on the type of the charging means and the desired method sequence filling of the reactor 11 may take place pressureless or under pressure. With pressureless filling the phosphide can easily be introduced into the reactor with the feed screw 17. An exact quantity determination is possible with the balance 15 disposed beneath the reactor 11. The expansion of the liquid carbon dioxide to be introduced via the valve 12 into the reactor 11 can take place in such a manner that due to the expansion carbon dioxide ice forms with a layer of which the phosphide can be covered as described in example 1. Finally, by a correspondingly modified water feed means 18 water ice may also be placed in a layer onto the carbon dioxide ice. By way of the heat-exchange jacket 13 of the reactor 11 by supplying corresponding media if required a heating of the introduced contents of the now closed reactor can take place. After liquefying the carbon dioxide ice and the water ice the reaction course can now be accelerated by the agitator 16. When the reaction is completely finished the disinfestation fluid produced can be removed under expansion from the reactor and separated in the water separator 20 from excess reaction water. The disinfestation gas is then supplied via the connected means described above directly to the container to be fumigated.

With a closed mode of operation the reactor 11 can also be charged under pressure with the phosphide via an appropriate pressure lock. Carbon dioxide and water are in this case preferably metered in in liquid form. This can be done continuously or also batchwise. The necessary state conditions of the participating substances are then to be correspondingly set.

Figure 3:
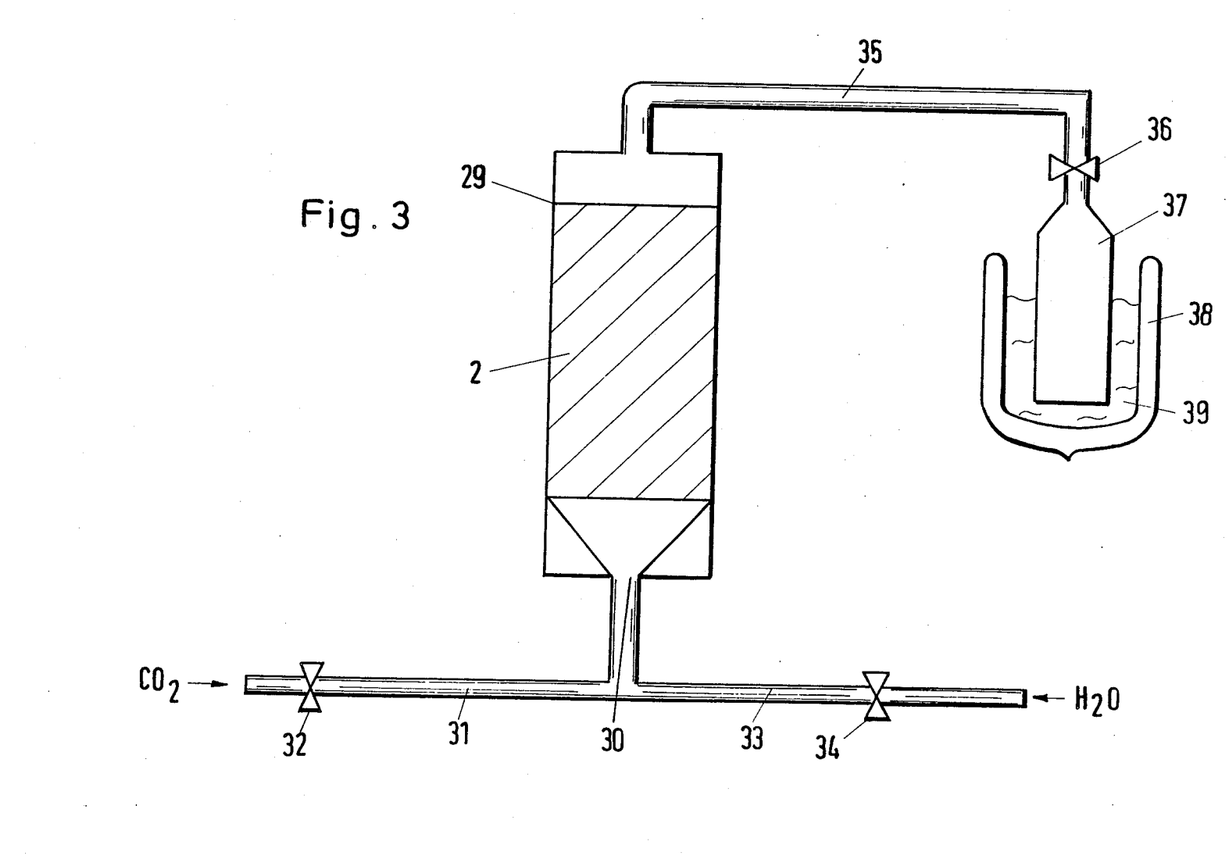
FIG. 3 is a schematic illustration of an extraction method.

A continuous method variant for making a phosphide-containing disinfestation fluid is illustrated in FIG. 3. This is the hydrolysis of metal phosphides in a closed apparatus by liquid carbon dioxide to which the required amounts of water are added by injection. Since at another point of the apparatus the two gases can be separated by fractionated distillation and the carbon dioxide returned to the process this continuous hydrolysis can also be referred to as "extraction" of phosphine from the metal phosphides.

FIG. 3 shows a vertical reactor 29 which is filled in its centre region with magnesium phosphide 2. At its lower end the reactor 29 has a liquid inlet 30 to which two conduits are connected, i.e. on the one hand a conduit 31 with a valve 32 for supplying carbon dioxide and on the other hand a conduit 33 with a valve 34 for supplying $H_2O$. At its upper end the reactor 29 is provided with an extraction conduit 35 for the disinfestation fluid, said conduit being connected via a valve 36 to a condensation container 37 which in turn is in a cooling jacket 38 which is filled with a coolant, that is liquid nitrogen, effecting the condensation of the disinfestation gas.

In the example of embodiment a flow of the magnesium phosphide with carbon dioxide and water is provided from the bottom to the top. A flow through in the opposite direction would also be conceivable. Into the liquid supply means 30 from the conduits 31 and 33 by means of the valves 32 and 34 predetermined amounts of liquid carbon dioxide and liquid water are metered. The mixture of the two liquids takes place before entrance into the reactor. As a variant it is alternatively possible to supply the two liquids to the lower reactor end separately and to allow them to mix only there. At the upper end from the column 29 the disinfestation fluid formed by the reaction with the phosphide is extracted in liquid manner although on corresponding expansion it may also be gaseous and in the example of embodiment introduced into a condensation vessel in the form of a steel cylinder which serves as transport container for the disinfestation fluid. To obtain the disinfestation fluid in the steel cylinder as liquid again a condensation at correspondingly low temperatures is necessary and this can be achieved by cooling by means of liquid nitrogen.

In the so-called "extraction methods" described here it may be advantageous to operate in the supercritical region of the carbon dioxide. The reactor 10 must then be designed as pressure container to take operating pressures between 80 and 100 bar. Although liquid carbon dioxide itself ensures in this method variant a favourable mass and heat transport, the carbon dioxide has an even better mobility in the supercritical state.

By measurements of the phosphine concentration in the disinfestation fluid produced and accordingly controlling the water metering the process can easily be kept under control. On condensation of the disinfestation gas into the steel cylinder 37 additional carbon dioxide may be added for dilution in order to obtain in the steel cylinder a disinfestation fluid which is in a concentration ready for use.

Figure 4:
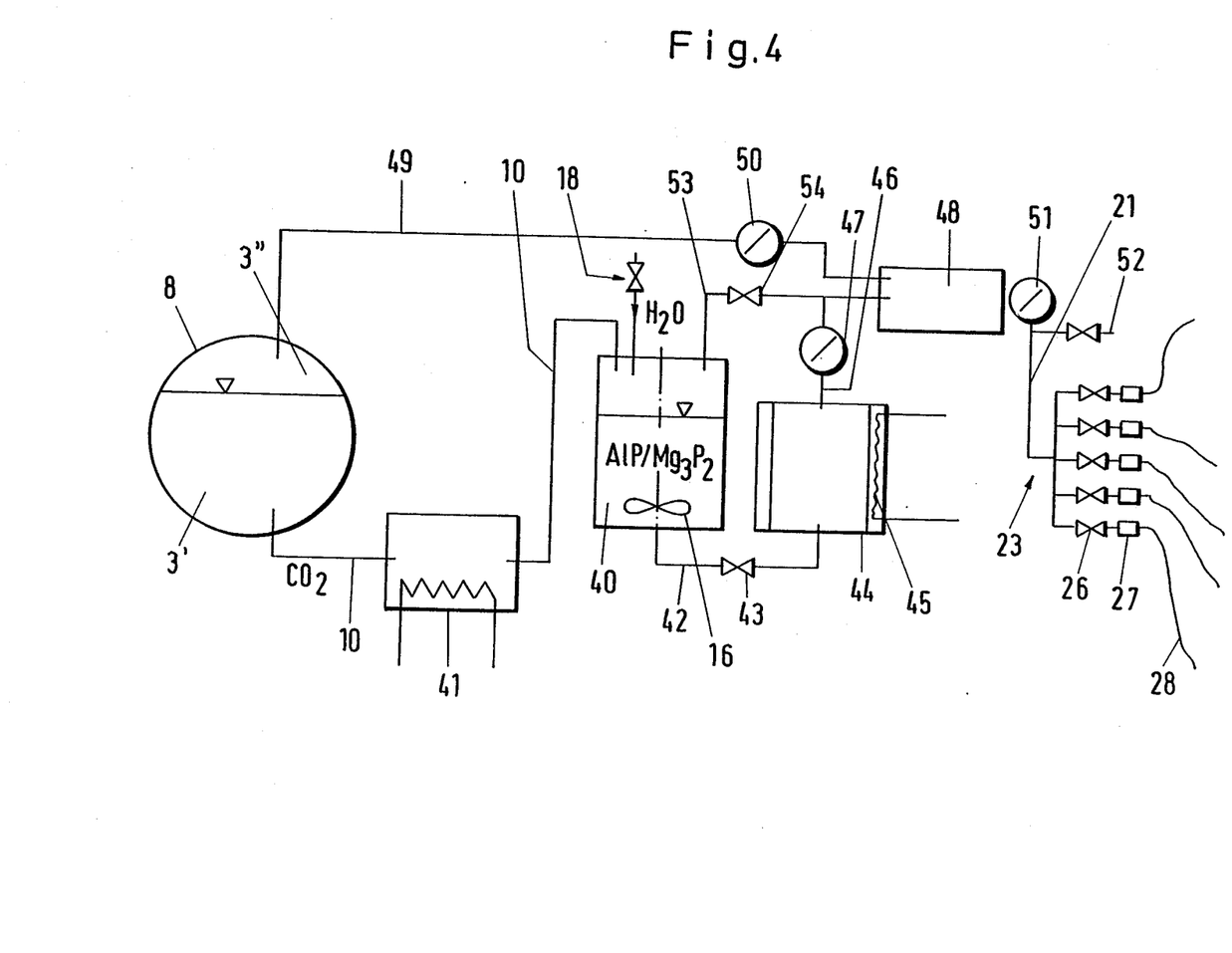
FIG. 4 is a method scheme of an apparatus for carrying out the extraction method.

FIG. 4 shows the scheme of an apparatus which in modification of the apparatus according to FIG. 2 can be operated for the continuous production of the disinfestation fluid by the extraction method described above. Components corresponding to the scheme of FIG. 2 are denoted by the same reference numerals.

In the supply container 8 liquid carbon dioxide is stored preferably at a pressure of 70 bar. The $CO_2$ supply container is connected via a conduit 10 for liquid $CO_2$ to a reactor 40. Into the conduit 10 an indirect heat exchanger 41 is also inserted. With the aid of this heat exchanger the temperature of the liquid carbon dioxide can be set to a predetermined value before entry into the reactor 40. If the operation is to be carried out in the supercritical range of carbon dioxide generally a heating of the carbon dioxide must be carried out in the heat exchanger 41. In this example of embodiment the carbon dioxide conduit 10 is introduced into the upper end of the reactor. A first extraction conduit 42 for the disinfestation fluid leaves the reactor 40 at the lower end so that in this embodiment the operation can be carried out with downwardly flowing media. A supply means 18 for supplying $H_2O$ to the reactor 40 is also disposed at the upper end of said reactor 40. Said means is designed for metered supply of liquid water. The facilities for charging the reactor with aluminium phosphide or magnesium phosphide are not shown in this method scheme. It is possible to fill the reactor 40 in the opened state once with phosphide and then to allow the operation to take place continuously until the amount of phosphide is used up. The gasification residues are then removed from the reactor and the reactor is filled again. It would of course also be conceivable to introduce the phosphide continuously by means of a rotation lock or the like.

The first extraction conduit 42 is connected via a valve 43 to a collecting container 44. The collecting container 44 is provided with a heat-exchange jacket 45 for use when required. A cooling may be necessary if the disinfestation fluid generated is to be kept in the liquid state at reduced pressure. This is for example necessary when a liquid filling of the disinfestation fluid in the container is provided.

At the upper end of the collecting container 44 an extraction conduit 46 is provided which leads via a quantity meter 47 to a mixing porportioning container 48. Via said conduit 49 disinfestation liquid coming from the collecting container 44 can be diluted in the mixing proportioning container 48 to a necessary use concentration. Via a conduit 21, which again contains a quantity meter 51, the disinfestation gas is supplied to a distribution conduit system 23 corresponding to that of FIG. 2. The conduit 21 also contains an extraction connecting piece 52 which can serve for taking samples of the finished disinfestation gas for analysis purposes.

From the upper part of the reactor 40 a conduit 53 leads via a valve 54 likewise into the mixing proportioning container 6.

The apparatus described permits of various modes of operation for the part following the reactor 40. If without intermediate storage the disinfestation gas is to be supplied to the distribution conduit system 23 for direct use the disinfestation gas generated in the reactor 40 can be extracted via the head conduit 53 and the expansion valve 54 and supplied to the mixing proportioning container 48. The valve 43 at the lower end of the reactor then remains closed. Dilution of the disinfestation gas generated can take place with gaseous $CO_2$ which is supplied via the conduit 49 to the mixing proportioning container 48. If the disinfestation fluid is to be withdrawn in liquid form the conduit 42 at the lower end of the reactor is used. With appropriate cooling the disinfestation fluid can be stored in the collecting container 44. It can be withdrawn therefrom after certain storage via an expansion valve (not shown) and the conduit 46 and likewise supplied to the mixing proportioning container 48. The conduit 53 can also be employed to return disinfestation gas from the conduit 46 to the reactor 40 if further concentration with phosphide is desired.

Figure 5:
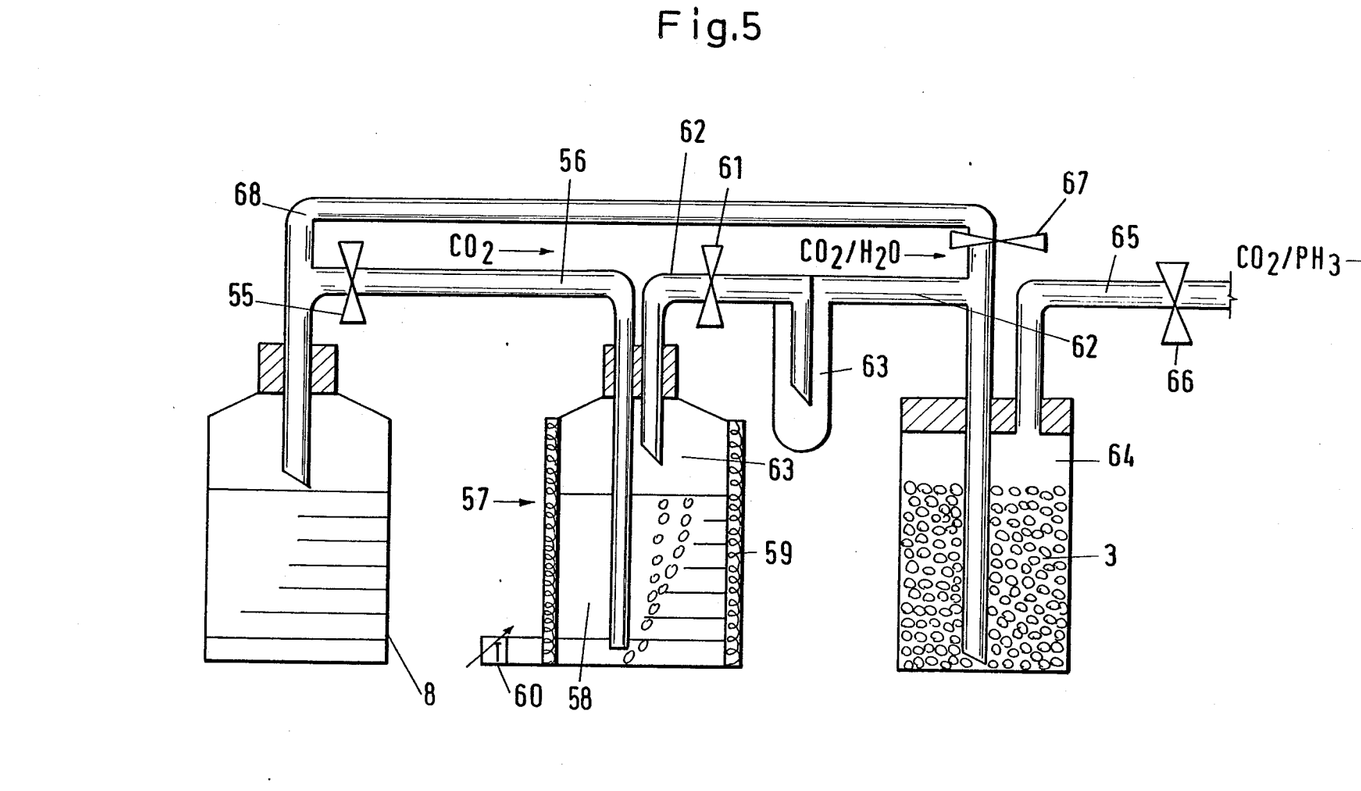
FIG. 5 is a schematic method representation for a continuous method using $CO_2$ saturated with water vapor and FIG. 6 is a method scheme of an apparatus for carrying out the method of FIG. 5.

A preferred variant of the method described is represented by the so-called gas method. The method procedure is schematically illustrated in FIG. 5. In this method variant, which operates with gaseous carbon dioxide, for water proportioning into the carbon dioxide the fact that the saturation amount of carbon dioxide gas for water vapor is different at different temperatures is utilized.

In the schematic method representation of FIG. 5 the gas space of a $CO_2$ supply container 8 is connected via a conduit 56 provided with an expansion valve 55 to a water container 57 into the water filling 58 of which the conduit 56 extends. The water container 57 is surrounded by a heating jacket 59 which is provided with a temperature regulator 60. A continuation conduit 62 provided with a valve 61 for the gaseous carbon dioxide starts in the gas space 63 of the water container 57 above the level of the water surface 58. The conduit leads further via a liquid separator 63 to a reactor 64. The reactor 64 contains a packing of magnesium phosphide 3 into which the conduit 62 leads. A conduit 65, provided with a valve 66, for the disinfestation gas generated in the reactor 64 leaves the reactor at the upper end thereof. Finally, a bypass conduit 68 is provided which has a valve 67 and which connects the gas space of the $CO_2$ supply container 8 directly to the conduit 62 which leads into the magnesium phosphide packing of the reactor 64.

The method sequence is as follows: via the conduit 56 gaseous $CO_2$ is extracted from the supply container 8 and conducted through the water filling 58 of the water container 57. In the latter the carbon dioxide gas becomes saturated with $H_2O$. Since the amount of saturation depends on the temperature of the gas it can be set by means of specific temperature regulation of the water amount 58 with the heating jacket 59 and the temperature regulator 60 so that a carbon dioxide gas having a quite specific water vapor amount is supplied to the reactor 64 for the reaction with the magnesium phosphide 3. This arrangement not only affords an elegant possibility of controlling the water amount supplied to the reaction but can also be operated with high safety because on overshooting of the reaction in the reactor 64, which manifests itself in a pronounced temperature increase, via the bypass conduit 68 carbon dioxide gas which is not directly charged with water vapor can be supplied to the reactor to retard the reaction.

The reaction rate between the carbon dioxide gas charged with the water vapor and the metal phosphide provided depends on the rate of the gas flow, i.e. the contact time, the reactivity of the metal phosphide, the basicity of the metal ions and the temperature. Thus, aluminium phosphide tends to form a basic rather than a tertiary carbonate and this in turn affects the stoichiometry of the reaction of the water vapor to form phosphine. Since carbon dioxide cools on evaporation a constant transport of cold to the water container 57 takes place and to maintain a specific temperature said container must therefore continuously be heated. The temperature obtaining in the water cylinder also clearly governs the water content of the carbon dioxide and the reaction rate and thus the phosphine content of the resulting gas mixture. The method variant described here has the following advantages:

control of the reaction rate via the water vapor saturation, continuous subjection of the reaction mixture to inert gas in high excess and pressureless generation of a directly usable gas mixture.

EXAMPLE 2

On complete conversion corresponding to the theoretical reaction equation given above with a method sequence according to FIG. 5 and with carbon dioxide gas saturated with water vapor the following phosphine contents result in vol. % in the disinfestation gas forming, in dependence upon the temperature of the water container:

| T °C.: | 5 | 10 | 15 | 20 | 25 | 30 | 35 | 40 | 45 |
|---|---|---|---|---|---|---|---|---|---|
| Vol %: | 0.57 | 0.84 | 1.22 | 1.75 | 2.48 | 3.46 | 4.79 | 6.56 | 8.89 |

For fumigating an object of 10000 m³ volume with a phosphide dosing of 500 ppm v/v phosphine and a water temperature in the water container 57° of 25° C. a phosphine concentration in the carbon dioxide gas is obtained of about 2.5 vol. %. For fumigating the object about 200 m³ of the disinfestation gas (2 vol. % of the object volume) is necessary, corresponding to a carbon dioxide amount of 360 to 370 kg. In this amount of disinfestation gas 7000 g phosphine are contained, corresponding to the dose indicated above.

Figure 6:
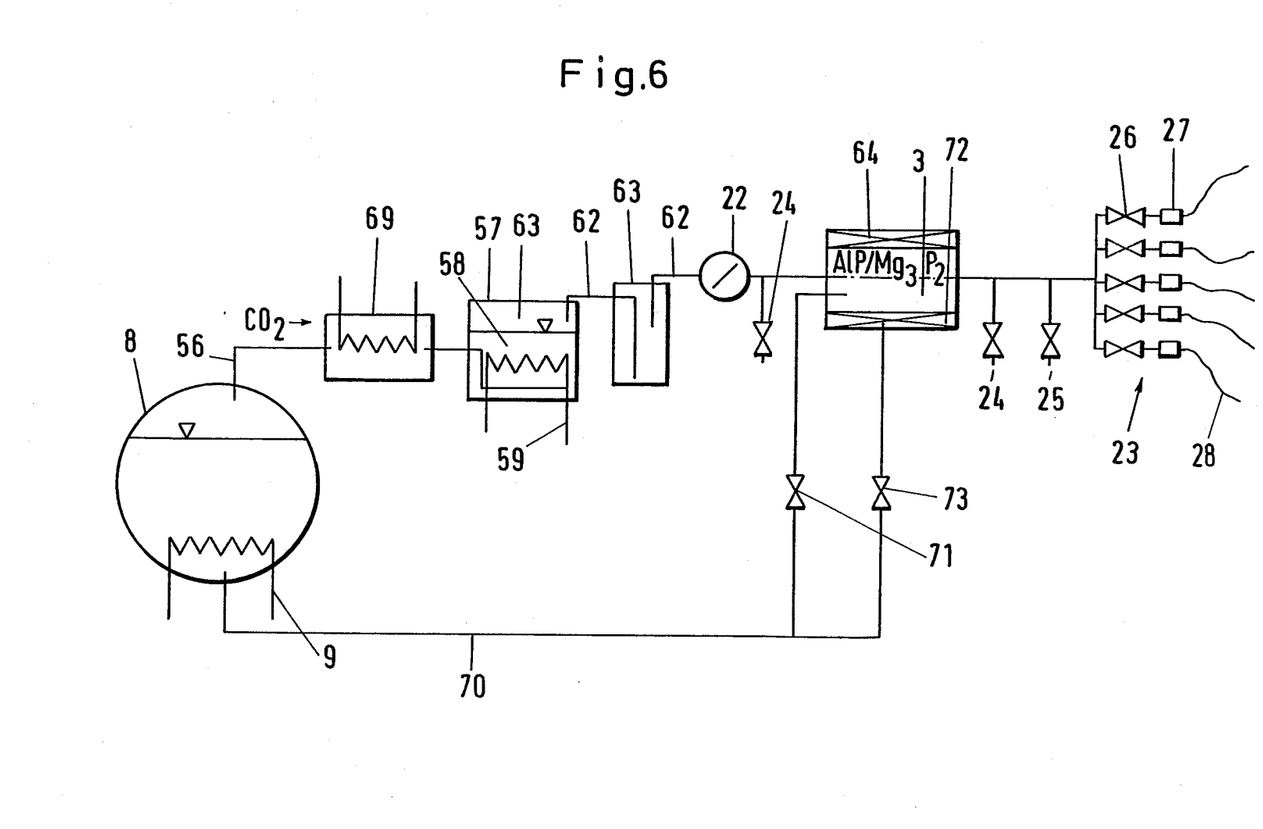

FIG. 6 is a schematic illustration of an apparatus which operates by the method described in conjunction with FIG. 5. In the conduit 56 for gaseous $CO_2$ which leads out of the gas space of the supply container 8 to the water container 57 an indirect heat exchanger 69 is also provided. Furthermore, the supply container 8 is provided with a heating means 9. Since by the expansion of the carbon dioxide gas cold is continuously transported to the water container 57, i.e. heat continuously withdrawn from the contents thereof, the heating 59 in the water container 57 is generally not sufficient to hold the water temperature at a desired value. It is therefore expedient to preheat the carbon dioxide in the supply container 8 itself and in the additional heat exchanger 69 before it passes to the water container 57 for saturation with water vapor. Behind the water separator 63 there is a flow meter 22 for controlling the amount of carbon dioxide gas supplied to the reactor 64. A bypass conduit 70 for supplying additional carbon dioxide gas to the reactor 64 is connected in this example of embodiment to the liquid space of the carbon dioxide supply container 8. Said conduit contains for this purpose an expansion valve 71 to allow the carbon dioxide to enter the reactor 63 in gaseous state. The reactor 64 itself is additionally provided with a cooling jacket 72 to which via a branch conduit 73 from the conduit 70 in addition liquid or expanded gaseous carbon dioxide can be supplied for cooling.

We claim:

1. Method of preparing a disinfestation fluid in a controlled manner which contains an inert fluid and phosphine obtained from the hydrolysis of a water-decomposable metal phosphide, characterized in that $H_2O$ is added to the inert fluid in a controlled amount to produce an inert fluid/$H_2O$ mixture, said amount of $H_2O$ being that which is necessary for controlled hydrolysis of said metal phosphide, the inert fluid/$H_2O$ mixture is brought into contact with the metal phosphide for a reaction therebetween and the resulting disinfestation fluid formed in said reaction is separated from solid reaction residue formed in said reaction.

2. Method according to claim 1, characterized in that as inert fluid nitrogen, argon or helium in fluid state is used.

3. Method according to claim 1, characterized in that as inert fluid carbon dioxide in fluid state is used.

4. Method according to claim 1, characterized in that a mixture of the inert fluid in the liquid state and liquid water is brought into reaction contact with the metal phosphide.

5. Method according to claim 4, characterized in that in a reaction chamber from the bottom to the top firstly a predetermined amount of the metal phosphide, inert fluid in the solid state and an amount of water ice adequate for the complete reaction of the metal phosphide are layered over each other, the reaction chamber sealed pressure-tight and brought into temperature equalization with the ambient temperature, the solidified inert fluid first changing into the liquid state with concomitant pressure increase, mixing with water from the melting water ice and bringing the water into contact with the metal phosphide for the reaction.

6. Method according to claim 5, characterized in that the mixture consisting of inert fluid and phosphine is withdrawn from the reaction chamber in gaseous state.

7. Method according to claim 5, characterized in that after the reaction has taken place and prior to removing disinfestation fluid from the reaction chamber a concentration of not more than 10 vol. % phosphine arises.

8. Method according to claim 4, characterized in that in a pressure-tight apparatus the amount of liquid water necessary for the reaction sequence is injected into the liquid or supercritical inert fluid extracted continuously from a supply pressure container and said mixture is conducted into an extraction column which contains the metal phosphide and from which the resulting disinfestation fluid is removed.

9. Method according to claim 8, characterized in that the disinfestation fluid is collected under pressure in a collecting container.

10. Method according to claim 8, characterized in that the liquid or supercritical inert fluid after removal from the supply container is conducted for adjusting a predetermined reaction temperature through a heat exchanger.

11. Method according to claim 8, characterized in that the disinfestation fluid is removed from the extraction column or the collecting container with pressure relaxation as disinfestation gas and supplied to the further use.

12. Method according to claim 11, characterized in that the disinfestation gas prior to further use is diluted by supplying a further gaseous inert fluid to a desired phosphine concentration.

13. Method according to claim 11, characterized in that the disinfestation gas is deposited for storage and transport with the aid of a suitable indirectly applied coolant into sealable pressure bottles.

14. Method according to claim 11, characterized in that on direct further use of the disinfestation gas for fumigating containers the remaining inert fluid is returned to the process.

15. Method according to claim 1, characterized in that the inert fluid is charged in the gaseous state with water vapor and said gas mixture is conducted through the metal phosphide.

16. Method according to claim 15, characterized in that the inert gas for absorbing water vapor is conducted through liquid water.

17. Method according to claim 16, characterized in that the amount of liquid water is temperature-regulated.

18. Method according to claim 15, characterized in that to the metal phosphide additionally dry inert gas is supplied for controlling the reaction course.

19. Method according to claim 15, characterized in that the reaction chamber containing the metal phosphide is temperature-regulated.

20. Method according to claim 15, characterized in that the disinfestation gas obtained by the reaction of the metal phosphide is supplied directly to the further use.

21. Method according to claim 15, characterized in that when using carbon dioxide as inert gas the water vapor amount in the carbon dioxide gas and further reaction parameters are controlled such that the disinfestation gas does not contain more than 10 vol. % phosphine.

* * * * *